United States Patent [19]

Yuasa et al.

[11] Patent Number: 4,891,456
[45] Date of Patent: Jan. 2, 1990

[54] METHOD FOR PREPARING NORBORNENE STRUCTURE COMPOUND

[75] Inventors: Hitoshi Yuasa; Mitsuo Matsuno, both of Yokohama; Tetsuo Satoh, Tokyo, all of Japan

[73] Assignee: Nippon Oil Co., Ltd., Tokyo, Japan

[21] Appl. No.: 213,547

[22] Filed: Jun. 30, 1988

[30] Foreign Application Priority Data

Jul. 6, 1987 [JP] Japan .................................. 62-166868

[51] Int. Cl.$^4$ ............................ C07C 5/02; C07C 5/05
[52] U.S. Cl. ...................................... 585/275; 585/271
[58] Field of Search ............................ 585/22, 271, 275

[56] References Cited

U.S. PATENT DOCUMENTS 4,271,323  6/1981  Durand et al. ...................... 585/275
4,675,459  6/1987  Yuasa et al. ........................... 585/22

FOREIGN PATENT DOCUMENTS 1233129  5/1971  United Kingdom ................. 585/275

Primary Examiner—Curtis R. Davis
Attorney, Agent, or Firm—Malcolm B. Wittenberg

[57] ABSTRACT

A method for preparing a norbornene structure compound comprises hydrogenating a compound represented by the formula of

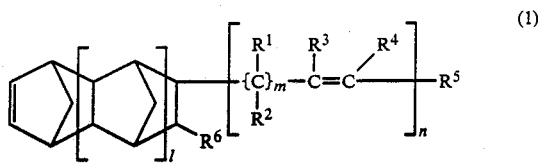

wherein l, m and n are integers of $0 \leq l \leq 3$, $0 \leq m \leq 8$ and $1 \leq n \leq 3$, respectively, and each of $R^1$ to $R^6$ is a hydrogen atom or a hydrocarbon residue having 1 to 3 carbon atoms with or without $R^6$ forming a ring with $R^4$ or $R^5$, in the presence of a Ziegler type catalyst containing in combination a compound of a transition metal of Groups IV to VI of the periodic table and an organometallic compound of Groups I to III of the periodic table, to thereby convert the compound of the formula (1) into a compound represented by the following formula of

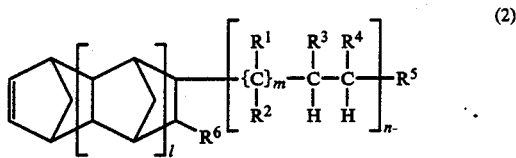

wherein l, m and n are the same as above.

8 Claims, No Drawings

METHOD FOR PREPARING NORBORNENE STRUCTURE COMPOUND

BACKGROUND OF THE INVENTION

This invention relates to a method for preparing a norbornene structure compound that can be employed as an intermediate product for preparation of medical or agricultural chemicals or as a monomer for preparation of polymers.

The norbornene structure compound represented by the formula (2)

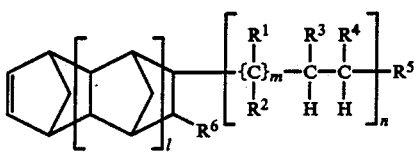
(2)

wherein l, m and n are integers of $0 \leq l \leq 3$, $0 \leq m \leq 8$ and $1 \leq n \leq 3$, respectively, and each of $R^1$ to $R^6$ is a hydrogen atom or a hydrocarbon residue having 1 to 3 carbon atoms and $R^6$ may form a ring with $R^4$ or $R^5$, has an active double bond of norbornene ring and can be converted into useful medicines or agricultural chemicals upon addition of a variety of organic or inorganic compounds to this double bond. Also the compound represented by the formula (2) may be employed alone or in combination with other olefins as a monomer for cationic or coordinated anionic polymerization or for ring-opening polymerization employing metathesis catalysts. Recently, there is an increasing demand for polymers that are prepared from the above mentioned monomers and that may be useful for optical applications, such as optical disks, or for polymers prepared upon thermal or cationic polymerization which polymers exhibit superior weather- and heat-resistance, transparency and color on account of not having unsaturated bonds. However, the compounds (2) that can be used for these usage cannot be prepared without considerable difficulties. There is so far known a method for preparing the compound of the formula (2) by the Diels-Alder reaction of cyclopentadiene or a compound capable of producing cyclopentadiene in the reaction system, such as dicyclopentadiene, with monoolefins, such as butene-1, pentene-1, pentene-2, cyclopentene, hexene-1, hexene-2, hexene-3, 3-methyl-1-butene, 2-methyl-2-pentene, 3-methylcyclohexene, 2-methyl-2-hexene, 3-methyl-2-hexene, ethylnorbornene, n-propylnorbornene, isopropylnorbornene, ethyl-1,4,5,8-dimethano-1,2,3,4,4a,5,8,8a-octahydronaphthalene, n-propyl-1,4,5,8-dimethano-1,2,3,4,4a,5,8,8a-octahydronaphthalene, isopropyl-1,4,5,8-dimethano-1,2,3,4,4a,5,8,8a-octahydronaphthalene, 2,3,3a,4,7,7a-hexahydro-4,7-methano-1H-indene, 2,3,3a,4,4a,5,8,8a,9,10-decahydro-4,9,5,8-dimethano-1H-benzindene, as exemplified in the following equations (3) to (6).

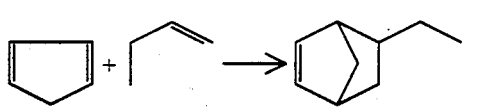
(3)

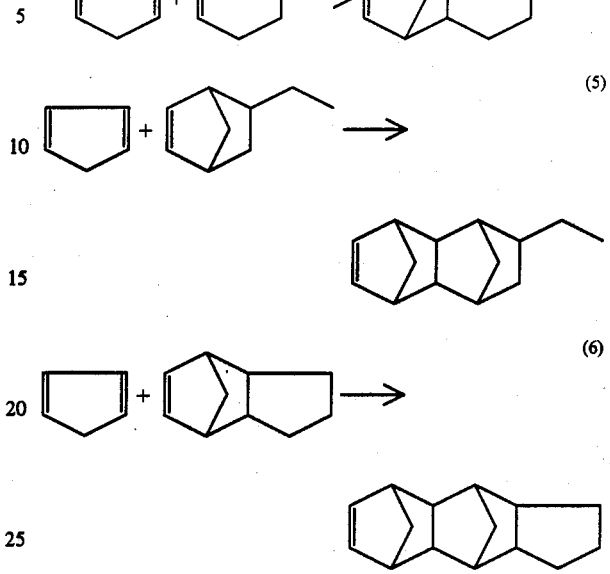

The practical example of synthesis for ethylnorbornene and pentylnorbornene has been reported by Plate (Dokl. Akad. Nauk. SSSR, 105,989,991 (1955)) and that for endo- and exo-2,3,3a,4,7,7a-hexahydro-4,7-methano-1H-indene has been reported by Bruson et al. in Journal of American Chemical Society, vol. 67, pp723(1945) and vol. 70, pp2809(1948) et al.

However, in the Diels-Alder reaction between cyclopentadiene and monoolefin, the reaction rate is extremely low because no electron-withdrawing substituents are bonded to monoolefin, then the reaction has to be carried out at elevated temperature for a long time to raise the yield. To make matters worse, since the reaction is carried out under these hostile conditions, trimers, tetramers, pentamers or higher polymers of cyclopentadiene, or addition product of cyclopentadiene to the object compound represented by the formula (2), are by-produced in larger quantities, thus adversely affecting the selectivity of the object compound.

On the other hand, in the Diels-Alder reaction of cyclopentadiene and conjugated or non-conjugated polyene, double bonds not involved in the reaction with these polyenes act as electron-withdrawing groups, in a manner different from the aforementioned reaction of monoolefin as the reactant, such that the reaction rate is increased and the compound having the formula (1)

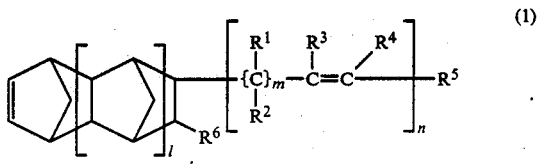
(1)

wherein l, m and n are the same as those for the formula (2), can be produced easily. For example, dimerization of cyclopentadiene according to the formula (7)

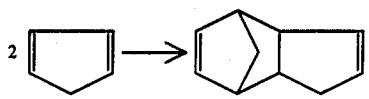

proceeds rapidly at an ambient temperature, while 5-vinyl bicyclo [2. 2. 1] hept-2-ene and tricyclopentadiene according to the formulae (8) and (9)

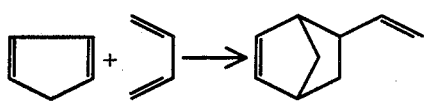

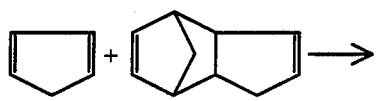

may be produced easily at 60° to 150° C. The same may be said of the reaction shown by the formula (10)

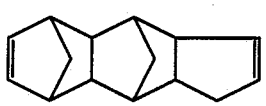

It may be contemplated that the object compound represented by the formula (2) may be prepared by hydrogenation of the compound of the formula (1) that can be produced easily as described above. However, it was not possible with the conventional methods to produce the compound of the formula (2) with high selectivity. According to East German Patent No. 106,343 or report of I. S. Kolominkov (Izv. Akad. Nauk. SSSR, Ser. Khim, 1972 (5)1180), 5-vinyl bicyclo [2. 2. 1] heptane (A) is selectively produced by hydrogenation of 5-vinyl bicyclo [2. 2. 1] hept-2-ene as shown by the formula (11)

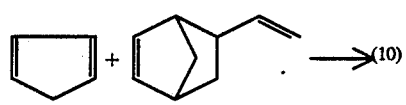

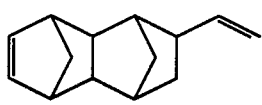

but the object compound of 5-ethyl bicyclo [2. 2. 1] hept-2-ene (B) is not produced. According to Japanese Patent Publications Nos. 34811/1973 and 45391/1976, Japanese Laid-open Patent Publications Nos.4158/1976 and 95648/1977 and reports by C. A. Brown (J. Chem. Soc.,D,1969(17),952), upon hydrogenation of dicyclopentadiene or tricyclopentadiene, a mixture of 2,3,3a,4,7,7a-*hexahydro*-4,7-methano-1H-indene (C) and 3a,4,5,6,7,7a-hexahydro-4,7-methano-1H-indene (D), as shown by the formula (12)

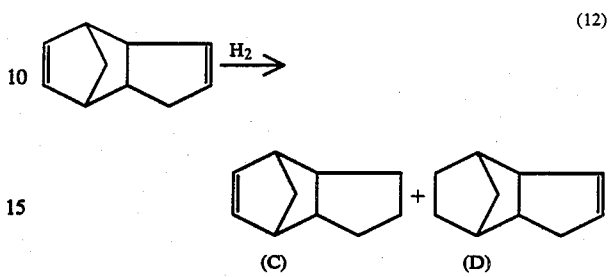

is obtained, but the compound D accounts for the major portion of the product and the object compound (C) is produced only in minor quantities.

It is reported by Yu. G. Osokin et al in Dokl. Akad. Nauk. SSSR, 220 (4), 851(1975), Ser. Khim that, upon hydrogenation of 5-vinyl bicyclo [2. 2. 1 ] hept-2-ene, 5-ethyl bicyclo [2. 2. 1 ] hept-2-ene is produced in a slightly larger amount than 5-vinylbicyclo [2. 2. 1] heptane. It is also reported by W. Keim et al. in Chem.-Ing.-Tech., vol. 55, pp906(1983) that, with hydrogenation of dicyclopentadiene, the yield ratio of (C)/(D) in the formula (12) of the order of 5/4 may be obtained, while it is reported by K. M. Nicholas in Journal of American Chemical Society, vol. 97, pp3254 (1975) that the object compound (C) may be obtained by a method of protecting the highly reactive double bond at the 5 and 6 positions of dicyclopentadiene with an iron carbonyl compound. It is apparent that the methods shown in these reports provide improved selectivity in comparison with the preceding examples in consideration of the difference in reactivities between the two double bonds. However, it is still not possible with these methods to produce the compound of the formula (2) with high selectivity or to produce the compound on an industrial scale.

On the other hand, Ziegler type catalysts are known to exhibit hydrogenation acitivity, as reported in detail in "Homogeneous Hydrogenation", page 363, by B. R. James, J. Wiley & Sons, New York, 1973.

However, it has not so far been known that the compound represented by the formula (1) may be hydrogenated to the compound represented by the formula (2) with high selectivity in the presence of the Ziegler type catalyst.

SUMMARY OF THE INVENTION

It is a principal object of the present invention to provide a method for preparing a norbornene structure compound represented by the formula (2) from the compound represented by the formula (1) easily and with higher selectivity.

The above and other objects of the present invention will become apparent from the following description.

In accordance with the present invention, there is provided a method for preparing a norbornene structure compound comprising hydrogenating a compound represented by the formula of

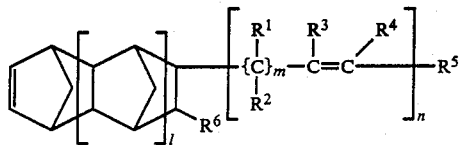

(1)

wherein l, m and n are integers of $0 \leq l \leq 3$, $0 \leq m \leq 8$ and $1 \leq n \leq 3$, respectively, and each of $R^1$ to $R^6$ is a hydrogen atom or a hydrocarbon residue having 1 to 3 carbon atoms, with or without $R^6$ forming a ring with $R^4$ or $R^5$, in the presence of a Ziegler type catalyst containing in combination a compound of a transition metal of Groups IV to VI of the periodic table and an organometallic compound of Groups I to III of the periodic table, to thereby convert the compound of the formula (1) into a compound reprsented by the following formula of

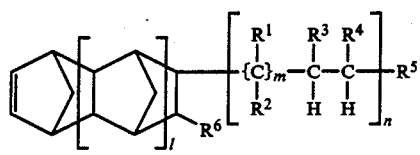

(2)

wherein l, m and n and $R^1$ to $R^6$ are the same as above.

DESCRIPTION OF THE PREFERRED EMBODIMENTS

The present invention will be explained in futher detail.

According to the present invention, a compound represented by the formula (2)

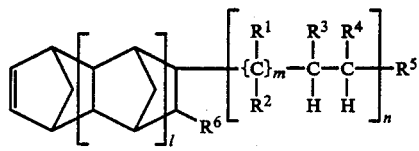

(2)

can be prepared by hydrogenation of a compound represented by the formula (1)

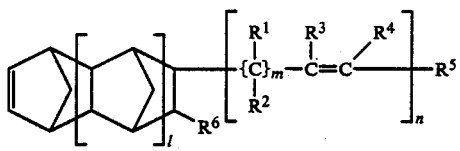

(1)

in the presence of a Ziegler type catalyst containing in combination an organic compound of a transition metal of the Groups IV to VI of the periodic table and an organometallic compound of the Groups I to III of the periodic table. In the above formula, l, m and n are integers of $0 \leq l \leq 3$, $0 \leq m \leq 8$ and $1 \leq n \leq 3$, respectively, each of $R^1$ to $R^6$ is a hydrogen atom or a hydrocarbon residue having 1 to 3 carbon atoms, and $R^6$ may form a ring with $R^4$ or $R^5$. The object compound for $l > 3$, $m > 8$ or $n > 3$ or with $R^1$ to $R^6$ having not less than four carbon atoms cannot be provided because of difficulties in manufacture.

The compounds employed in accordance with the present invention and represented by the formula (1) may be enumerated by dicyclopentadiene, tricyclopentadiene, tetracyclopentadiene, 5-vinylbicyclo [2. 2. 1] hept-2-ene, 2-vinyl-1,4,5,8-dimethano-1,2,3,4,4a,5,8,8a-octahydronaphthalene, 5-propenylbicyclo [2. 2. 1] hept-2-ene, 2-propenyl-1,4,5,8-dimethano-1,2,3,4,4a,5,8,8a-octahydronaphthalene, 5-isopropenyl bicyclo [2. 2. 1] hept-2-ene, 2-isopropenyl-1,4,5,8-dimethano-1,2,3,4,4a,5,8,8a-octahydronaphthalene, 5-methyl-6-vinyl bicyclo [2. 2. 1] hept-2-ene, 2-methyl-3-vinyl-1,4,5,8-dimethano-1,2,3,4,4a,5,8,8a-octahydronaphthalene, 5-(1-butenyl)-bicyclo [2. 2. 1] hept-2-ene, 2-(1-butenyl)-1,4,5,8-dimethano-1,2,3,4,4a,5,8,8a-octahydronaphthalene, 5-(2-butenyl)-bicyclo [2. 2. 1] hept-2-ene, 2-(2-butenyl)-1,4,5,8-dimethano-1,2,3,4,4a,5,8,8a-octahydronaphthalene, 5-methyl-6-propenyl bicyclo [2. 2. 1] hept-2-ene, 2-methyl-3-propenyl-1,4,5,8-dimethano-1,2,3,4,4a,5,8,8a-octahydronaphthalene, 1,4-methano-1,4,4a,7,8,8a-hexahydronaphthalene, 1,4-methano-1,4,4a,5,8,8a-hexahydronaphthalene, 1,4,5,10-dimethano-1,4,4a,5,5a,8,9,9a,10,10a-decahydroanthracene, and 1,4,5,10-dimethano-1,4,4a,5,5a,6,9,9a,10,10a-decahydroanthracene.

The Ziegler type catalyst employed in the present invention is of a system containing in combination a compound of a transition metal of the Groups IV to VI of the periodic table and an organometallic compound of the Groups I to III of the periodic table. The compounds of the transition metal may be typified by organic and/or inorganic compounds of Ti, Zr, Hf, V, Cr, Mo or W and preferably of Ti, Zr, Hf or V. The compounds of the transition metal include alkoxides such as titanium ethoxide, titanium isopropoxide, titanium butoxide, zirconium ethoxide, zirconium isopropoxide, zirconium butoxide, hafnium ethoxide, hafnium butoxide, vanadium ethoxide, vanadium isopropoxide, vanadium butoxide, vanadyl ethoxide, vanadyl isopropoxide or vanadyl butoxide, and halides such as titanium trichloride, titanium tribromide, titanium triiodide, titanium tetrachloride, titanium tetrabromide, titanium tetraiodide, zirconium tetrachloride, zirconium tetrabromide, zirconium tetraiodide, hafnium tetrachloride, hafnium tetrabromide, vanadium chloride, vanadium tetrabromide, vanadyl chloride, vanadyl bromide, vanadyl monoethoxydichloride or vanadyl diethoxymonochloride. Acetylacetonatoes such as titanium acetylacetonato, zirconium acetylacetonato, hafnium acetylacetonato, vanadium acetylacetonato, or vanadyl acetylacetonato, carbonyl compounds such as vanadium hexacarbonyl, cyclopentadienyl metal carbonyls such as bis-cyclopentadienyl titanium dicarbonyl or cyclopentadienyl vanadium tetracarbonyl, bis-cyclopentadienyl compounds such as bis-cyclopentadienyl titanium dichloride, bis-cyclopentadienyl vanadium dichloride or a bis-cycloentadienyl titanium dimer, and alkyl complex compounds of methyltitanium trichloride, may also be emloyed as the transition metal compounds.

These transition metal compounds may also be supported on suitable carriers such as $Al_2O_3$, $MgO$, $MgCl_2$ or $SiO_2$. It is also preferred that the carriers be previously processed with electron donors.

The organometallic compounds of the Groups I to III may include for example organo-alkali metal compounds, such as methyl lithium, ethyl lithium, n-propyl lithium, n-butyl lithium, sec-butyl lithium, cyclohexyl lithium, phenyl lithium, benzyl lithium, phenyl sodium, benzyl sodium, naphthalene sodium, triphenyl methyl sodium, phenyl potassium, butadiene potassium, styrene potassium or naphthalene potassium, organic compounds of an alkaline earth metal such as methyl magnesium chloride, ethyl magnesium bromide, n-butyl magnesium choride, butyl magnesium iodide, phenyl magnesium chloride, vinyl magnesium chloride, allyl magnesium chloride, diethyl magnesium, dibutyl magnesium, methyl zinc iodide, ethyl zinc iodide, n-propyl zinc iodide, dimethyl zinc, diethyl zinc, dibutyl zinc, dimethyl cadmium, diethyl cadmium, dibutyl cadmium or diphenyl cadmium, and organic compounds of a Group III metal, such as trimethyl aluminum, triethyl aluminum, triisobutyl aluminum, tricyclohexyl aluminum, diethyl aluminum chloride, ethyl aluminum sesquichloride, ethyl aluminum dichloride or diethyl ethoxyaluminum.

The present invention may be carried out in the absence of solvents or in the presence of solvents not interfering with the reaction. These solvents may include hydrocarbon solvents such as hexane, heptane, octane, cyclohexane, decalin, benzene, toluene or xylene, ethers such as diethyl ether, diisopropyl ether, dibutyl ether, tetrahydrofuran, tetrahydropyran, diphenyl ether, glyme or diglyme. Halogenated hydrocarbons such as chlorobenzene may also be used depending on the kinds of the organometal compounds employed. Although indene and norbornadiene may be also used as solvents, these may be used more appropriately as ligands for improving the selectivity for the present reaction.

The concentration of the substrate of the present reaction may be selected freely in the range of from about 0.1 mol/liter to a value corresponding to the non-solvent state.

It is preferred that the transition metal compound of the catalyst be used in a molar ratio ranging from 0.0001 to 0.10, and preferably from 0.001 to 0.05 based on one mole of the compound represented by the formula (1). With the use of the transition metal compound in excess of the above range, the reaction rate and heat evolution are increased such that it is difficult to control the reaction conditions and increased costs are involved in the post-processing following the completion of the reaction. The molar ratio of the transition metal compound to the organometallic compound is preferably in the range of from 1:3 to 1:100, more preferably in the range of from 1:3 to 1:20, and most preferably 1:5 to 1:10.

It is preferred that hydrogen of higher purity be employed, while the presence of oxidating impurities, such as oxygen, is desirably avoided. Although the hydrogen employed in the reaction may be at subatmospheric pressure, the hydrogen pressure is preferably in the range of from 0 to 100 kg/cm$^2$ G and more preferably in the range of from 1 to 20 kg/cm$^2$ G.

The reaction temperature may be in the range of from $-30°$ to $200°$ C. and preferably from $0°$ to $100°$ C.

The end point of the reaction may be selected freely. In general, the compound represented by the formula (1) is difficult to isolate from the compound represented by the formula (2) since they differ from each other only by the presence or absence of two hydrogen atoms. Thus, one may proceed in such a fashion that the conversion be raised to the utmost so that the amount of the compound of the formula (1) is decreased and only the compound of the formula (2) is effectively obtained. Alternatively, the reaction may be stopped at an optionally seleted conversion reaction of, for example 80%, and the reaction product may be used as a mixture of the compounds (1) and (2). Still alternatively, the unreacted feedstock may be converted into other compounds easy to separate by any known methods. Thus, the reaction may be stopped when the condition most favorable from economical considerations are satisfied.

EXAMPLES OF THE INVENTION

The description with reference to several specific examples of the present invention is given hereinbelow. It should be noted that the scope of the prsent invention is by no means limited to the specific examples but any other mode may be adopted insofar as they are pursuant to the object of the invention.

EXAMPLE 1

1.5 millimoles of titanocene dichloride, 100 cc of benzene, 350 millimoles of 5-vinyl bicyclo [2. 2. 1] hept-2-ene and 15 millimoles of triethyl aluminum were charged into a fully dried autoclave having a capacity of 500 cc and filled with nitrogen. The reaction was caried out at a controlled reaction temperature of 50° C. and with the addition of hydrogen at a constant hydrogen pressure of 4 kg/cm$^2$ G. The results of analysis by gas chromatography after 6.5 hours have revealed that the conversion was 96.8% and the selectivity for 5-ethyl bicyclo [2. 2. 1] hept-2-ene was 85.2%. The catalyst was deactivated upon addition of methanol to the reactant and the solvent was distilled off, after which the remaining reactant was subjected to distillation under reduced pressure. It was found that there were no residues, which meant that there occurred no secondary reactions, such as oligomerization or polymerization.

EXAMPLE 2

The reaction was carried out in the same way as in Example 1, except that TiCl$_4$ was used as the catalyst. It was found upon analysis that the conversion was 33.7% and selectivity for 5-ethyl bicyclo [2. 2. 1] hept-2-ene was 62.3%.

EXAMPLE 3

The reaction was carried out in the same way as in Example 1 except that n-butyl lithium was employed in place of triethyl aluminum. The conversion was 95.4% and selectivity for 5-ethyl bicyclo [2. 2. 1] hept-2-ene was 83.7%.

EXAMPLE 4

The reaction was carried out in the same way as in Example 1 except that 15 millimoles (7.5 cc) of n-butyl magnesium chloride having a concentration equal to 2M was used as the catalyst in place of triethyl aluminium and the reaction was continued for 1.5 hours. The conversion was 98.5% and selectivity for 5-ethyl bicyclo [2. 2. 1] hept-2-ene was 78%.

EXAMPLE 5

The reaction was carried out in the same way as in Example 1 except that 10 wt. % of TiCl$_4$ carried on MgCl$_2$ was used as the catalyst component and the reaction was continued at 94° C. for nine hours. The conversion was 97% and selectivity for 5-ethyl bicyclo [2. 2. 1] hept-2-ene was 59%.

EXAMPLE 6

The reaction was carried out in the same way as in Example 1 except that zirconocene hydride chloride was used as the catalyst component and the raction was continued at 70° C. for four hours. The conversion was 57% and selectivity for 5-ethyl bicyclo[2. 2. 1] hept-2-ene was 43%

EXAMPLE 7

The reaction was carried out in the same way as in Example 1 except using vanadyl acetylacetonato as the catalyst. The conversion was 38% and selectivity for 5-ethyl bicyclo [2. 2. 1] hept-2-ene was 47%.

EXAMPLE 8

The reaction was carried out in the same way as in Example 1 except using a bicyclopentadienyl titanium dimer as the catalyst. The conversion was 97% and selectivity for 5-ethyl bicyclo [2. 2. 1] hept-2-ene was 81%.

EXAMPLE 9

The reaction was carried out in the same way as in Example 1 except that dicyclopentadiene was used as the substrate, 0.5 millimole of titanocene dichloride and 8 millimoles of triethyl aluminum were used and the reaction was continued for 4.3 hours. The conversion was 89.9% and selectivity for 2,3,3a,4,7,7a-hexahydro-4,7-methano- 1H-indene was 66.3%.

EXAMPLE 10

The reaction was carried out in the same way as in Example 1 except using tricyclopentadiene as the substrate. The conversion was 63% and selectivity for 2,3,3a,4,4a,5,8,8a,9,10-decahydro-4,9,5,8-dimethano-1H-benzindene was 57.1%.

EXAMPLE 11

The reaction was carried out in the same way as in Example 1 except that 17 millimoles of titanocene dichloride and 75 millimoles of triethyl aluminum was used and reacted at 40° C.

The conversion was 93.4% and selectivity for 5-ethyl bicyclo[2. 2. 1 ]hept-2-ene was 96.5%.

It will be seen that, by hydrogenating the compound of the formula (1) in the presence of a Ziegler catalyst, the compound of the formula (2) can be produced easily with improved selectivity.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A method for preparing a norbornene structure compound comprising hydrogenating a compound represented by the formula of

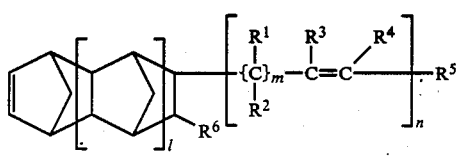

(1)

wherein l, m and n are integers of $0 \leq l \leq 3$, $0 \leq m \leq 8$ and $1 \leq n \leq 3$, respectively, and each of $R^1$ to $R^6$ is a hydrogen atom or a hydrocarbon residue having 1 to 3 carbon atoms with or without $R^6$ forming a ring with $R^4$ or $R^5$, in the presence of a Ziegler type catalyst containing in combination a compound of a transition metal of Groups IV to VI of the periodic table and an organometallic compound of Groups I to III of the periodic table, to thereby convert the compound of the formula (1) into a compound represented by the following formula of

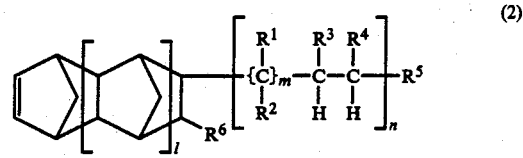

(2)

wherein l, m and n are the same as above.

2. The method according to claim 1 wherein the compound represented by the formula (1) is selected from the group consisting of dicyclopentadiene, tricyclopentadiene, tetracyclopentadiene, 5-vinylbicyclo [2. 2. 1] hept-2-ene, 2-vinyl-1,4,5,8-dimethano-1,2,3,4,4a,5,8,8a-octahydronaphthalene, 5-propenyl-bicyclo [2. 2. 1] hept-2-ene, 2-propeny-1,4,5,8-dimethano-1,2,3,4,4a,5,8,8a-octahydronaphthalene, 5-isopropenyl bicyclo[2. 2. 1] hept-2-ene, 2-isopropenyl-1,4,5,8-dimethano-1,2,3,4,4a,5,8,8aoctahydronaphthalene, 5-methyl-6-vinylbicyclo[2. 2. 1] hept-2-ene, 2-methyl-3-vinyl-1,4,5,8-dimethano-1,2,3,4,4a,5,8,8a -octahydronaphthalene, 5-(1-butenyl)-bicyclo [2. 2. 1] hept-2-ene, 2-(1-butenyl)-1,4,5,8-dimethano-1,2,3,4,4a,5,8,8aoctahydronaphthalene, 5-(2-butenyl)-bicyclo [2. 2. 1] hept-2-ene, 2-(2-butenyl)-1,4,5,8-dimethano-1,2,3,4,4a,5,8,8aoctahydronaphthalene, 5-methyl-6-propenylbicyclo [2. 2. 1] hept-2-ene, 2-methyl-3-propenyl-1,4,5,8,-dimethano-1,2,3,4,4a,5,8,8aoctahydronaphthalene, 1,4-methano-1,4,4a,7,8,8ahexahydronaphthalene, 1,4-methano-1,4,4a,5,8,8ahexahydronaphthalene, 1,4,5,10-dimethano-1,4,4a,5,5a,8,9,9a,10,10a-decahydroanthracene, 1,4,5,10-dimethano-1,4,4a,5,5a,6,9,9a,10,10a-decahydroanthracene and mixtures thereof.

3. The method according to claim 1 wherein said compound of the transition metal is selected from the group consisting of titanium ethoxide, titanium isopropoxide, titanium butoxide, zirconium ethoxide, zirconium isopropoxide, zirconium butoxide, hafnium ethoxide, hafnium butoxide, vanadium ethoxide, vanadium isopropoxide, vanadium butoxide vanadyl ethoxide, vanadyl isopropoxide, vanadyl butoxide, titanium trichloride, titanium tribromide, titanium triiodide, titanium tetrachloride, titanium tetrabromide, titanium tetraiodide, zirconium tetrachloride, zirconium tetrabromide, zirconium tetraiodide, hafnium tetrachloride, hafnium tetrabromide, vanadium chloride, vanadyl tetrabromide, vanadyl chloride, vanadyl bromide, vanadyl monoethoxydichloride, vanadyl diethoxymonochloride, titanium acetylacetonato, zirconium acetylacetonato, hafnium acetylacetonato, vanadium acetylacetonato, vanadyl acetylacetonato, vanadium hexacarbonyl, bis-cyclopentadienyl titanium dicarbonyl, cyclopentadienyl vanadium tetracarbonyl, bis-cyclopentadienyl titanium dichloride, bis-cyclopentadienyl vanadium dichloride, a bis-cycloentadienyl titanium dimer, methyltitanium trichloride and mixtures thereof.

4. The method according to claim 1 wherein said organometallic compound of the Groups I to III is selected from the group consisting of methyl lithium, ethyl lithium, n-propyl lithium, n-butyl lithium, sec-butyl lithium, cyclohexyl lithium, phenyl lithium, benzyl lithium, phenyl sodium, benzyl sodium, naphthalene sodium, triphenyl methyl sodium, phenyl potassium, butadiene potassium, styrene potassium, naphthalene potassium, methyl magnesium chloride, ethyl magnesium bromide, n-butyl magnesium choride, butyl magnesium iodide, phenyl magnesium chloride, vinyl magnesium chloride, allyl magnesium chloride, diethyl magnesium, dibutyl magnesium, methyl zinc iodide, ethyl zinc iodide, n-propyl zinc iodide, dimethyl zinc, diethyl zinc, dibutyl zinc, dimethyl cadmium, diethyl cadmium, dibutyl cadmium, diphenyl cadmium, trimethyl aluminum, triethyl aluminum, triisobutyl aluminum, tricyclohexyl aluminum, diethyl aluminum chloride, ethyl aluminum sesquichloride, ethyl aluminum dichloride, diethyl ethoxyaluminum and mixtures thereof.

5. The method according to claim 1 wherein the molar ratio of said transition metal compound to the compound of the formula(1) ranges from 0.0001:1 to 0.10:1.

6. The method according to claim 1 wherein the molar ratio of said transition metal compound to said organometallic compound ranges from 1:3 to 1:100.

7. The method according to claim 1 wherein the hydrogenation is carried out under a hydrogen pressure of 0 to 100 kg/cm$^2$ G.

8. The method according to claim 1 wherein the hydrogenation is carried out at $-30°$ to $200°$ C.

* * * * *